United States Patent
Shenai-Khatkhate et al.

(10) Patent No.: US 6,770,769 B2
(45) Date of Patent: Aug. 3, 2004

(54) TRIALKYLINDIUM PREPARATION

(75) Inventors: Deodatta Vinayak Shenai-Khatkhate, Danvers, MA (US); Michael Brendan Power, Newburyport, MA (US); Ronald L. DiCarlo, Jr., Newfields, NH (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 10/407,993

(22) Filed: Apr. 5, 2003

(65) Prior Publication Data

US 2003/0191333 A1 Oct. 9, 2003

Related U.S. Application Data

(60) Provisional application No. 60/370,713, filed on Apr. 6, 2002.

(51) Int. Cl.$^7$ .................................................. C07F 5/00
(52) U.S. Cl. .......................................................... 556/1
(58) Field of Search ............................................. 556/1

(56) References Cited

U.S. PATENT DOCUMENTS

| | | |
|---|---|---|
| 4,847,399 A | 7/1989 | Hallock et al. |
| 5,015,750 A | 5/1991 | Tran et al. |
| 5,756,786 A * | 5/1998 | Power et al. .................. 556/1 |

OTHER PUBLICATIONS

John J. Eisch, "Organometallic Compounds of Group III. I. The Preparation of Gallium and Indium Alkyls from Organoaluminum Compounds", Journal of the American Chemical Society, vol. 84, No. 19, Oct. 17 1962, pp. 3605–3610.

G. Laube et al., "Me, In Preparation and Zone Refining of Adducts for High Quality InP and GaInAs MOVPE", Journal of Crystal Growth, North Holland Amsterdam, 1988, pp. 45–51.

* cited by examiner

*Primary Examiner*—Porfirio Nazario-Gonzalez
(74) *Attorney, Agent, or Firm*—S. Matthew Cairns

(57) ABSTRACT

Trialkylindium compounds are prepared by reacting indium trihalide with a trialkylaluminum compound in the presence of a fluoride salt, wherein the molar ratio of the indium trihalide to the fluoride salt is at least 1:4.5. Such trialkylindium compounds are particularly suitable for use in metalorganic vapor phase epitaxy.

11 Claims, No Drawings

TRIALKYLINDIUM PREPARATION

This application claims the benefit of Provisional Application No. 60/370,713, filed Apr. 6, 2002.

BACKGROUND OF THE INVENTION

The present invention relates generally to the field of organometallic compounds. In particular, the present invention relates to certain trialkylindium compounds suitable for use in indium vapor deposition processes.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), and chemical beam epitaxy ("CBE"). Chemical vapor deposition processes, such as metalorganic chemical vapor deposition ("MOCVD"), deposit a metal layer by decomposing organometallic precursor compounds at elevated temperatures, i.e., above room temperature, and either at atmospheric pressure or at reduced pressures.

A wide variety of metals may be deposited using such CVD or MOCVD processes. See, for example, Stringfellow, *Organometallic Vapor Phase Epitaxy: Theory and Practice*, Academic Press, $2^{nd}$ Edition, 1999, for an overview of such processes. For example, indium is used in a variety of metal films produced by epitaxial growth, particularly in the manufacture of electronic devices such as integrated circuits and light emitting diodes ("LEDs"). Exemplary indium containing metal films include indium-phosphide ("InP"), indium-gallium-arsenide ("InGaAs"), indium-gallium-aluminum-phosphide ("InGaAlP"), indium-gallium-arsenic-phosphide ("InGaAsP"), indium-gallium-arsenide/gallium-arsenide/aluminum-gallium-arsenide ("InGaAs/GaAs/AlGaAs"), indium-arsenide ("InAs"), indium-antimonide ("InSb") and indium-arsenic-bismuthide ("InAsBi").

Metal layers and alloy layers are typically formed in CVD or MOCVD processes by the decomposition of one or more precursor compounds. A wide variety of precursor compounds may be used. In conventional CVD processes, suitable precursor compounds must have a sufficient vapor pressure to allow them to be transported to the deposition chamber.

Trialkylindium compounds have achieved commercial success as indium sources in vapor phase deposition of indium and indium-containing films. In particular, trimethylindium is the preferred indium source in the formation of indium-phosphide films which are useful in the semiconductor and related electronic industries. Trialkylindium compounds must be highly purified, i.e. substantially free of detectable levels of metallic impurities such as tin, silicon, germanium and zinc, to be useful in such electronic applications. One method for producing highly purified indium source compounds is that disclosed in U.S. Pat. No. 4,847,399 (Hallock et al.). This patent discloses a process for preparing trimethylindium that is very low in metallic impurities, however, such process requires the use of methyl lithium and ether as the reaction solvent. Trace amounts of ether invariably remain associated with the trimethylindium produced by this method.

One of the important uses for trialkylindium compounds, and the primary use for highly purified trialkylindium compounds, is as indium sources for the vapor deposition of indium-containing films in the manufacture of LEDs. Oxygen, if present in any of the metal source compounds, becomes incorporated into the crystal lattice of the film being grown where it contributes excess electrons which can reduce the intensity of light produced by LEDs. Accordingly, trialkylindium compounds having high purity, 5-nines purity with respect to metallic impurities, and extremely low oxygen content are desired.

U.S. Pat. No. 5,756,786 (Power et al.) discloses a process for preparing trimethylindium having high purity without the use of ethereal solvents. This process uses an alkyl exchange reaction between a trihaloindium compound and a trialkylaluminum compound in the presence of a metal fluoride, wherein the molar ratio of the trihaloindium compound to metal fluoride is 1:6. Such a large amount of metal fluoride salt increases the handling and disposal costs of reaction byproducts. In addition, the purification procedure in this patent requires the trimethylindium to be molten, thereby heightening safety and handling concerns.

There is a continuing need for methods of preparing trialkylindium compounds in high yield and purity, while improving the handling and safety associated with such methods and reducing the amount of material for disposal.

SUMMARY OF THE INVENTION

It has been surprisingly found that trialkylindium compounds can be prepared using a reduced amount of metal fluoride salt as compared to conventional methods and in a variety of solvents. The present preparation of trialkylindium compounds uses simple purification procedures which avoids molten trialkylindium compounds. In addition, the present invention provides trialkylindium compounds in high yield and high purity.

The present invention provides a method of manufacturing trialkylindium compounds including the steps of: a) reacting a trihaloindium compound with a trialkylaluminum compound in an organic reaction solvent in the presence of a fluoride salt to form a reaction mixture, wherein the molar ratio of the trihaloindium compound to the fluoride salt is at least 1:4.5, and wherein the organic reaction solvent has a boiling point of 100° C. or greater; b) separating the organic reaction solvent from the reaction mixture; and c) extracting the trialkylindium compound using an extraction solvent.

DETAILED DESCRIPTION OF THE INVENTION

As used throughout this specification, the following abbreviations shall have the following meanings, unless the context clearly indicates otherwise: ° C=degrees centigrade; NMR=nuclear magnetic resonance; g=gram; L=liter; mm=millimeters; mol=moles; and mL=milliliter.

"Halo" refers to fluoro, chloro, bromo and iodo. Likewise, "halogenated" refers to fluorinated, chlorinated, brominated and iodinated. "Alkyl" includes linear, branched and cyclic alkyl. The term "lower alkyl" refers to alkyl groups having 6 carbons or less. Unless otherwise noted, all amounts are percent by weight and all ratios are by weight. All numerical ranges are inclusive and combinable in any order, except where it is obvious that such numerical ranges are constrained to add up to 100%.

The present invention provides an indium compound suitable for use as a vapor deposition precursor compound, such as for CVD and/or MOCVD. Trialkylindium compounds are prepared by the process of the present invention which includes the first step of reacting a trihaloindium compound with a trialkylaluminum compound in an organic reaction solvent in the presence of a fluoride salt to form a reaction mixture, wherein the molar ratio of the trihaloindium compound to the fluoride salt is at least 1:4.5, and wherein the organic reaction solvent has a boiling point of 100° C. or greater.

A wide variety of trihaloindium compounds, having the formula $InX_3$ wherein X is a halogen, may be used in the present invention. While each "X" may be independently any halogen, it is preferred that each "X" is the same halogen. Particularly suitable trihaloindium compounds include, but are not limited to, trichloroindium, tribromoindium, triiodoindium and trifluoroindium, preferably trichloroindium, tribromoindium, and triiodoindium, and more preferably trichloroindium. The trihaloindium compounds are generally commercially available from a variety of sources or may be prepared by methods known in the art.

Trialkylaluminum compounds useful in the present invention typically have the formula $R_3Al$, wherein each R is independently selected from ($C_1$–$C_{10}$)alkyl, preferably ($C_1$–$C_6$)alkyl, and more preferably ($C_1$–$C_3$)alkyl. Suitable trialkylaluminum compounds include, but are not limited to, trimethylaluminum, triethylaluminum, tri-n-propylaluminum, tri-iso-propylaluminum, tri-iso-butylaluminum, tri-tert-butylaluminum, tri-n-butylaluminum, tri-n-hexylaluminum, and the like. Such trialkylaluminum compounds are generally commercially available from a variety of sources or may be prepared by a variety of methods known in the literature.

Any organic solvent that has a boiling point of 100° C. or greater, does not react with the reactants or the trialkylindium product, and that is free of ether-substitution may be used in the present invention. Particularly useful organic reaction solvents are aliphatic hydrocarbons and aromatic hydrocarbons. Suitable organic reaction solvents include, but are not limited to, mixtures of linear ($C_{10}$–$C_{12}$)alkyl benzenes ("LAB"), squalane, 1,2-dimethylnaphthalene, nonadecane, octadecane, heptadecane, hexadecane, pentadecane, eicosane, and the like. However, other high-boiling solvents, including saturated, unsaturated, straight-chain, branched, cyclic, and aromatic hydrocarbons, are also suitable.

A fluoride salt is added to the reaction mixture to aid in aluminum complex formation. A wide variety of fluoride salts may be used. Typically, the fluoride salt has the formula $MF_{n'}$, wherein M is tetra($C_1$–$C_4$)alkylammonium, tetra($C_6$–$C_{10}$)arylammonium, an alkali metal ion or an alkaline earth metal, and n' is the valence of the alkali or alkaline earth metal, i.e. n'=1 or 2. Preferably, the fluoride salt includes, but is not limited to, tetramethylammonium fluoride, tetraethylammonium fluoride, tetraphenylammonium fluoride, potassium fluoride, sodium fluoride, cesium fluoride, rubidium fluoride, lithium fluoride, calcium fluoride, barium fluoride, strontium fluoride and the like. Potassium fluoride is most preferred.

The molar ratio of the trihaloindium compound to the fluoride salt is at least 1:4.5. It will be appreciated by those skilled in the art that when the molar ratio of the trihaloindium compound to the fluoride salt is 1:6 or greater, a number of different purification/isolation methods for the trialkylindium compounds produced may be used, such as the sublimation approach described in U.S. Pat. No. 5,756,786. When a molar ratio of less than 1:6 is used, the trialkylindium compound cannot be isolated from the aluminum-fluoride complex using sublimation, as an organoaluminum fluoride compound also produced by the process co-sublimes with the desired trialkylindium product.

The extraction method of the present invention is particularly advantageous where sublimation cannot be used. Typically, the molar ratio of the trihaloindium compound to the fluoride salt is in the range of 1:4.5 to 1:6, preferably 1:4.5 to 1:5.9, and more preferably 1:4.5 to 1:5.5.

In one embodiment, where the fluoride salt is ammonium fluoride or an alkali metal fluoride, the present process provides trialkylindium compounds according to the following reaction scheme:

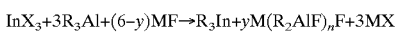

$InX_3 + 3R_3Al + (6-y)MF \rightarrow R_3In + yM(R_2AlF)_nF + 3MX$ where X=halogen, R=($C_1$–$C_{10}$)alkyl; M=ammonium or alkali metal ion; y=range 0 to 1.5 and n=1 to 2.

In general, the trihaloindium compound, fluoride salt and organic reaction solvent are added to a reaction vessel and the mixture is typically stirred and degassed. To this mixture is added the trialkylaluminum compound, usually in a dropwise manner. Following addition of the trialkylaluminum compound, the reaction mixture is typically heated, such as from 60° to 150° C.

In the second step of the present method, the organic reaction solvent is separated from the reaction mixture. Such solvent separation step may be accomplished by a variety of means, such as by atmospheric distillation, reduced pressure distillation, filtration and the like.

In the third step of the present method, the trialkylindium compound, the desired reaction product, is extracted from the organic reaction solvent or the reaction mixture through the use of an extraction solvent. Any extraction technique known in the art may suitably be used. For example, the organic reaction solvent may be removed completely, such as by distillation to yield a concentrated reaction mixture. Such reaction mixture may then be contacted with a solvent for the trialkylindium compound, or alternatively, a solvent for the unwanted material such as cyclopentane or cyclohexane, thereby leaving the trialkylindium compound. In another embodiment, the trialkylindium compound may be extracted from the organic reaction solvent using an extraction solvent. Any extraction solvent that dissolves the trialkylindium compound produced and does not dissolve the organoaluminum-fluoride salt is suitable. Exemplary extraction solvents include, but are not limited to, benzene, lower alkyl benzenes such as toluene, xylene including all isomers such as ortho-xylene, meta-xylene, and para-xylene, and trimethylbenzene including all its isomers, and the like.

When the trialkylindium compound is extracted into the extraction solvent, the desired trialkylindium compound is obtained by removing the extraction solvent such as by distillation. Alternatively, the trialkylindium compound may be crystallized from the extraction solvent by a variety of known methods. For example, when trimethylindium is prepared according to the present process and extracted using a mixture of linear alkyl benzenes, the trimethylindium may be crystallized from the linear alkyl benzene solution by slowly adding a small amount of a non-solvent, such as cyclopentane or cyclohexane. The trialkylindium compound may be purified after recovery/isolation from the extraction solvent. In general, trialkylindium compounds are purified by sublimation in the presence of a fluoride salt, particularly potassium fluoride, in a small amount of solvent, such as squalane.

A wide variety of trialkylindium compounds may be prepared according to the present process. Exemplary trialkylindium compounds have the formula $R_3In$, wherein each R is independently selected from ($C_1$–$C_{10}$)alkyl, preferably ($C_1$–$C_6$)alkyl, and more preferably ($C_1$–$C_3$)alkyl. Suitable trialkylindium compounds include, but are not limited to, trimethylindium, triethylindium, tri-n-propylindium, tri-iso-propylindium, tri-iso-butylindium, tri-tertbutylindium, tri-n-butylindium, tri-n-hexylindium, and the like.

The present process provides numerous advantages over conventional trialkylindium preparation methods. These advantages include: a reduction in fluoride salt use of about 25%, easier processing of post reaction by-products, lowered cost of raw materials per batch of trialkylindium compounds, increased capacity of trialkylindium manufacture, increased yield of trialkylindium compounds, increased rate of reaction, better handling of reaction products (solution instead of a suspension), improved safety due to dissolution of trialkylindium compounds in the organic reaction and extraction solvents which avoids neat molten trialkylindium compounds, and lower impurity incorporation in the final product. One disadvantage of conventional trialkylindium preparatory methods, such as those in U.S. Pat. No. 5,756,786, is that the high level of fluoride salt provides a suspension in the reaction vessel. Such suspension makes complete reaction of the starting materials difficult. In contrast, the present process provides a reaction mixture solution which provides easier handling and mixing of reaction components.

The trialkylindium compounds of the present invention are suitable for use as chemical vapor deposition and/or metalorganic chemical vapor deposition precursor compounds. The compounds of the present invention are substantially free of organic solvents, i.e. they contain ≦50 ppm of organic solvents and preferably ≦25 ppm of such solvents. The present trialkylindium compounds are preferably substantially free of detectable levels of silicon, tin, germanium and zinc, i.e. they contain <1 ppm of such impurities. Preferably, the present compounds are free of detectable levels of such impurities.

Indium films are typically deposited by first placing the desired indium precursor compound, or source compound, in a bubbler, or other delivery device suitable for delivering the present compounds in the gaseous phase having an outlet connected to a deposition chamber. A wide variety of bubblers may be used and are well-known to those skilled in the art. The particular bubbler will depend in part on the particular deposition apparatus used. The source compound is maintained in the bubbler as a liquid or solid. Solid source compounds are typically liquefied or sublimed prior to transportation to the deposition chamber. The source compound is typically transported to the deposition chamber by passing a carrier gas through the bubbler. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from about 300° to about 1000° C., the exact temperature selected being optimized to provide efficient deposition. Such optimization is well within the ability of one skilled in the art. Optionally, the temperature in the deposition chamber as a whole can be reduced if the substrate is maintained at an elevated temperature, or if other energy such as radio frequency ("RF") energy is generated by an RF source.

Suitable substrates for deposition may be any upon which a film including indium is desired, such as, but not limited to silicon such as silicon wafers used in integrated circuit manufacture, gallium arsenide, indium phosphate, and the like. Such substrates are particularly useful in the manufacture of integration circuits.

Deposition is continued for as long as desired to produce a film having the desired properties. Typically, the film thickness will be from several hundred to several thousand angstroms or more when deposition is stopped.

The present trialkylindium compounds are useful in depositing any film including indium or alloys thereof. Suitable films include, but are not limited to, indium, indium-phosphide ("InP"), indium-gallium-arsenide ("InGaAs"), indium-gallium-aluminum-phosphide ("InGaAlP"), indium-gallium-arsenic-phosphide ("InGaAsP"), indium-gallium-arsenide/gallium-arsenide/aluminum-gallium-arsenide ("InGaAs/GaAs/AlGaAs"), indium-arsenide ("InAs"), indium-antimonide ("InSb") and indium-arsenic-bismuthide ("InAsBi").

Thus, the present invention provides a method for depositing a film including indium on a substrate including the steps of: a) conveying a trialkylindium compound in the gaseous phase to a deposition chamber containing the substrate; b) decomposing the trialkylindium compound in the deposition chamber; and c) depositing a film including indium on the substrate.

Also provided by the present invention is a method for manufacturing an electronic device including the step of depositing a film including indium on an electronic device substrate including the steps of: a) conveying a trialkylindium compound in the gaseous phase to a deposition chamber containing the substrate; b) decomposing the trialkylindium compound in the deposition chamber; and c) depositing a film including indium on the substrate.

Suitable electronic devices include, but are not limited to, integrated circuits and light emitting diodes ("LEDs").

The following examples are presented to illustrate further various aspects of the present invention, but are not intended to limit the scope of the invention in any aspect.

EXAMPLE 1 (COMPARATIVE)

Indium chloride (10 g) and potassium fluoride ("KF") (13 g) and LAB (96 g) as the organic reaction solvent was charged into a 500 mL stainless steel flask equipped with a magnetic stir bar, and a U-Tube attached to a 500 mL three-necked flask and a reflux condenser. The contents were then degassed under full vacuum while maintained at 60° C. Trimethylaluminum (13 mL, 9.7 g) was transferred using a cannula stainless steel needle, in a dropwise manner to the reaction mass over a period of 15 minutes. The reaction mass was then heated to 118° C. The reaction mass turned from a grey suspension to a clear solution, which eventually deposited a white precipitate. The contents were then heated to 140° C. to ensure complete reaction. Upon completion of the reaction, the reaction mixture was easily stirred.

A crude product was obtained by sublimation at room temperature using full vacuum (7.5 g, 100% Yield). The NMR spectrum showed the product to be contaminated with 20% dimethylaluminum fluoride.

EXAMPLE 2 (COMPARATIVE)

Indium chloride (10 g) and KF (13 g) and squalane (60 g) as organic reaction solvent was charged into a 500 mL stainless steel flask equipped with a magnetic stir bar, and a U-Tube attached to a 500 mL three-necked flask and a reflux condenser. The contents were then degassed under full vacuum while maintaining the flask at 60° C. Trimethylaluminum (13 mL, 9.7 g) was transferred using a cannula stainless steel needle, in a dropwise manner to the reaction mass over a period of 15 minutes. The reaction mass was then heated to 140° C. to ensure complete reaction. Upon completion of the reaction mixture, stirring was more difficult than in Example 1.

A crude product was obtained by sublimation at full vacuum and at room temperature (7.5 g, 100% Yield). The NMR spectrum showed the product to be contaminated with 20% dimethylaluminum fluoride as in the case of Example 1.

EXAMPLE 3

Indium chloride (116 g) and KF (130 g) and LAB (1.5 L) as organic reaction solvent was charged into a 5 L stainless steel flask equipped with a mechanical stirrer, and a U-Tube attached to a 500 mL three-necked flask and a reflux condenser. The contents were then degassed under full vacuum while being maintained at 55° C. Trimethylaluminum (144 mL, 108 g) was added using an addition funnel, in a dropwise manner to the reaction mass over a period of 40 minutes. The content temperature was found to rise from 22.1° to 38.3° C. The contents were then heated to 140° C. to ensure complete reaction.

A crude product was obtained by sublimation at 39° C. using a full vacuum (100 g, >100% yield). The product was contaminated with dimethylaluminum fluoride as in the previous examples. The crude product was then washed with cyclopentane (300 mL) and sublimed from potassium fluoride (10 g) suspended in squalane (100 mL). Purified Trimethylindium (45 g, 56%) was obtained and confirmed by comparison with a spectrum of an authentic sample.

EXAMPLE 4

Indium chloride (116 g) and KF (130 g) are charged into a 5L stainless steel flask equipped with a mechanical stirrer, an addition funnel, and a reflux condenser. LAB as the organic reaction solvent (2 L) is next charged to the flask. Next, the contents are degassed under full vacuum while the temperature is maintained at 60° C. Trimethylaluminum (145 mL, 108 g) is next transferred into the addition funnel, and is then added in a dropwise manner to the reaction mass over a period of 1 hour. An exothermic reaction is found to occur. The reaction mass is heated to insure complete reaction.

The supernatent solution of trimethylindium in LAB is then separated from the solids in the reaction mass by filtration. Trimethylindium from the reaction residues is recovered by two successive extractions with toluene. The extracts are mixed with LAB solution of trimethylindium. The excess toluene is removed by atmospheric pressure distillation. To the concentrated solution in the distillation flask, cyclopentane (500 mL) is added in order to affect the crystallization. The crystalline product is then separated from the mother liquor by filtration. Further crops of crystals are obtained by further additions of the non-solvent cyclopentane to the concentrated mother liquor. The crude product obtained by filtration is then washed with pre-cooled cyclopentane in order to remove trace solvent impurities. The crude product is subjected to a vacuum distillation to obtain pure trimethylindium, which may be further purified by washing with cyclopentane and sublimation from potassium fluoride. High yields of trimethylindium are expected.

What is claimed is:

1. A method of manufacturing trialkylindium compounds comprising the steps of:
    a) reacting a trihaloindium compound with a trialkylaluminum compound in an organic reaction solvent in the presence of a fluoride salt to form a reaction mixture, wherein the molar ratio of the trihaloindium compound to the fluoride salt is at least 1:4.5, and wherein the organic reaction solvent has a boiling point of 100° C. or greater;
    b) separating the organic reaction solvent from the reaction mixture; and
    c) extracting the trialkylindium compound using an extraction solvent.

2. The method of claim 1 wherein the trihaloindium compound is chosen from trichloroindium, tribromoindium, and triiodoindium.

3. The method of claim 1 wherein the trialkylaluminum compound is chosen from trimethylaluminum, triethylaluminum, tri-n-propylaluminum, tri-iso-propylaluminum, tri-iso-butylaluminum, tri-tert-butylaluminum, tri-i-n-butylaluminum, and tri-n-hexylaluminum.

4. The method of claim 3 wherein the trialkylaluminum compound is trimethylaluminum.

5. The method of claim 1 wherein the organic reaction solvent is chosen from mixtures of linear ($C_{10}$–$C_{12}$)alkyl benzenes, squalane, 1,2-dimethylnaphthalene, nonadecane, octadecane, heptadecane, hexadecane, pentadecane, and eicosane.

6. The method of claim 1 wherein the organic reaction solvent is separated from the reaction mixture by distillation or filtration.

7. The method of claim 1 wherein the molar ratio of the trihaloindium compound to the fluoride salt is in the range of 1:4.5 to 1:6.

8. The method of claim 1 wherein the trialkylindium compound is extracted from the organic reaction solvent.

9. The method of claim 1 wherein the trialkylindium compound is chosen from trimethylindium, triethylindium, tri-n-propylindium, tri-iso-propylindium, tri-iso-butylindium, tri-tert-butylindium, tri-n-butylindium and tri-n-hexylindium.

10. The method of claim 9 wherein the trialkylindium compound is trimethylindium.

11. The method of claim 1 wherein the molar ratio of the trihaloindium compound to the fluoride salt is in the range of 1:4.5 to 1:5.9.

* * * * *